United States Patent [19]

Watjen et al.

[11] Patent Number: 5,102,885
[45] Date of Patent: Apr. 7, 1992

[54] IMIDAZOQUINOXALINE COMPOUNDS AND THEIR USE

[75] Inventors: Frank Watjen; Holger C. Hansen, both of Vaerlose, Denmark

[73] Assignee: Novo Nordisk A/S, Bagsvaerd, Denmark

[21] Appl. No.: 616,136

[22] Filed: Nov. 20, 1990

[30] Foreign Application Priority Data

Nov. 22, 1989 [DK] Denmark .................. 5883/89

[51] Int. Cl.⁵ .................. C07D 487/04; A61K 31/495
[52] U.S. Cl. ..................................... 514/250; 544/346
[58] Field of Search ..................... 544/346; 514/250

[56] References Cited

U.S. PATENT DOCUMENTS 4,999,354 3/1991 Hansen .................. 544/346

Primary Examiner—Mark L. Berch
Attorney, Agent, or Firm—Steve T. Zelson; Elias J. Lambiris

[57] ABSTRACT

New imidazoquinoxaline compounds having the general formula I

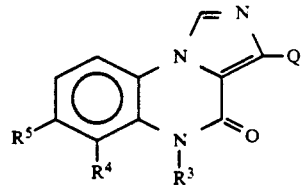

wherein

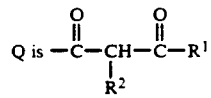

wherein $R^1$ and $R^2$ independently are hydrogen, straight or branched $C_{1-6}$-alkyl, or $C_{3-7}$-cycloalkyl; $R^3$ is hydrogen, straight or branched $C_{1-6}$-alkyl, straight or branched $C_{2-6}$-alkenyl, or aralkyl or aroylalkyl which may optionally be substituted with halogen or $C_{1-6}$-alkoxy; $R^4$ and $R^5$ independently are hydrogen, halogen, $C_{1-6}$-alkyl or trifluoromethyl.

The compounds are useful in psychopharmaceutical preparations as anticonvolusants, anxiolytics, hypnotics and in improving the cognitive function of the brain of mammals.

8 Claims, No Drawings

IMIDAZOQUINOXALINE COMPOUNDS AND THEIR USE

The present invention relates to therapeutically active imidazoquinoxaline compounds, a method of preparing the same, pharmaceutical compositions comprising the compounds, and to methods of treating therewith. The novel compounds are useful in psychopharmaceutical applications, e.g., in the treatment of central nervous system ailments, for example, as anticonvulsants or anxiolytics.

It is well known (Squires, R. F. and Braestrup, C. in Nature (London) 266 (1977) 732–734) that specific sites in the central nervous systems of vertebrates exhibit a high specific affinity for binding 1,4- and 1,5-benzodiazepines. These sites are called benzodiazepine receptors.

It has now been found that members of a novel group of imidazoquinoxaline compounds have strong affinity for the benzodiazepine receptors which make them useful in psychopharmaceutical preparations.

Accordingly, it is an object of the invention to provide such novel imidazoquinoxaline compounds.

The imidazoquinoxaline compounds having the general formula I

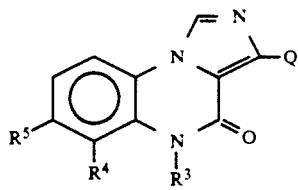

wherein

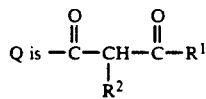

wherein $R^1$ and $R^2$ independently are hydrogen, straight or branched $C_{1-6}$-alkyl, or $C_{3-7}$-cycloalkyl; $R^3$ is hydrogen, straight or branched $C_{1-6}$-alkyl, straight or branched $C_{2-6}$-alkenyl, or aralkyl or aroylalkyl which may optionally be substituted with halogen or $C_{1-6}$-alkoxy; $R^4$ and $R^5$ independently are hydrogen, halogen, $C_{1-6}$-alkyl or trifluoromethyl.

The invention also relates to a method of preparing the above mentioned compounds. This method comprises:

a) reacting a reactive derivative of a compound having the general formula II

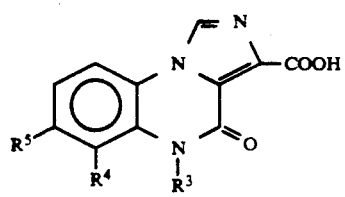

wherein $R^3$, $R^4$ and $R^5$ have the meanings set forth above, with a compound having the general formula III

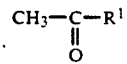

wherein $R^1$ has the meaning set forth above, to form a compound of the general formula IV

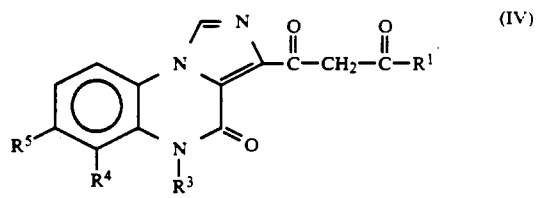

wherein $R^1$, $R^3$, $R^4$ and $R^5$ have the meanings set forth above, or b) alkylating a compound having the general formula IV

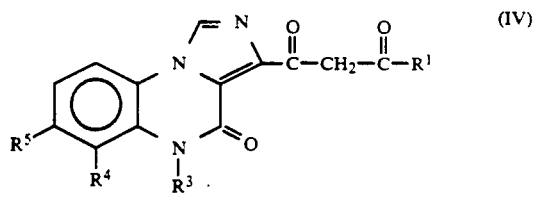

wherein $R^1$, $R^3$, $R^4$ and $R^5$ have the meanings set forth above, with an alkyl halide to form a compound of the general formula I

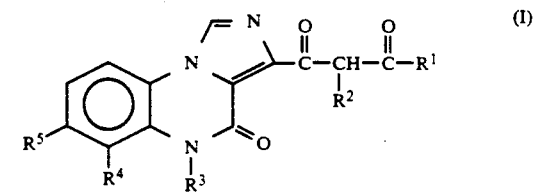

wherein $R^1$, $R^2$, $R^3$, $R^4$ and $R^5$ have the meanings set forth above.

The leaving group, Y, may be any suitable leaving group and, for example, those disclosed in U.S. Pat. Nos. 4,031,079 or 4,359,420, for example, halogen, alkylthio, e.g., methylthio, aralkylthio, N-nitrosoalkylamino, alkoxy, mercapto, -OP(O)(OR)$_2$ wherein R is lower-alkyl or -OP(O)(NR'R")$_2$ wherein R' and R" each represents lower-alkyl or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal, e.g., potassium or sodium, alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF) or the like. The temperature range employed may be any range suitable for the reaction to proceed at a reasonable rate and without undue delay or decomposition and a range from a minus forty (−40) degrees Celsius to about room temperature is accordingly usually particularly suitable.

The starting materials may be prepared from commercially available organic compounds and by using well known synthetic methods.

The pharmaceutical properties of the compounds of the invention can be illustrated by determining their capability for displacing radioactive labelled flunitrazepam from benzodiazepine receptors.

The displacement activity of the compounds of the invention may be found by determining the $ED_{50}$ value. The $ED_{50}$ value represents the dose (mg/kg) of a test substance which causes the specific binding of flunitrazepam to benzodiazepine receptors in a living brain to be reduced to 50% of the control value.

Such an in vivo test is carried out as follows:

Principle

Twenty minutes after a dose of $^3$H-flunitrazepam ($^3$H-FNM) (200 µCi/kg, i.v.) the amount of specific $^3$H-FNM binding to brain benzodiazepine receptors has reached its maximal value. This specific binding of $^3$H-FNM can be partly or completely prevented by simultaneous or prior administration of pharmacologically active benzodiazepines and by some benzodiazepine-like agents (Chang and Snyder, Eur.J. Pharmacol. 48, 212-218 (1978)).

Test procedure

Suspensions of test substances (2 mg/ml) are prepared in 5% Duphasol-X (TM Duphar, castor oil-ethylene oxide derivative for emulsifying and solubilizing oil and other water-insoluble substances) by sonification for 10 min using a Branson B15 microtip ultrasonifier (setting 7). Groups of three mice (female, NMR, 18-22 grams) are injected with the test substance at 100 mg/kg intraperitoneally. Fifteen minutes after test substance administration the mice are challenged with 4 µCi intravenously of $^3$H-FNM (70-90 Ci/mole) in 200 µl physiological saline. Twenty minutes after $^3$H-FNM administration mice are sacrificed by decapitation, the forebrains rapidly excised (within 30 sec) and homogenized in 12 ml of icecold 25 mM $KH_2PO_4$, pH 7.1, using an Ultra-Turrax homogenizer fitted with an N 10 shaft. Two aliquots of 1 ml are immediately filtered through Whatman GF/C glassfibre filters and washed with $2 \times 5$ ml of the above mentioned buffer. The amounts of radioactivity on the filters are determined by conventional scintillation counting. One group of untreated mice serves as control. One to three mice are injected with 25 µg/kg clonazepam i.p. 30 minutes before $^3$H-FNM to determine the amount of non-specific $^3$H-FNM binding, which should be between 8-15% of total binding. When doses of 100 mg/kg inhibit more than 50% of specific $^3$H-flunitrazepam binding; test substances are administered in doses, which are factors of 3.16 times lower than 100 mg/kg. The $ED_{50}$ for a test substance is defined as that dose which inhibits 50% of specific $^3$H-FNM binding. Specific binding is the amount of binding in controls minus the amount binding in clonazepam-treated mice.

Results

The $ED_{50}$ value is determined from dose response curves. If only one dose of test substance is administered the $ED_{50}$ value is calculated as follows, provided that the inhibition of specific binding is within the range of 25-75%:

$$ED_{50} = \text{(administered dose)} \times \frac{1}{\left[\frac{C_o}{C_x} - 1\right]} \text{ mg/kg}$$

where $C_o$ is specific binding in controls and $C_x$ is specific binding in mice treated with test substance.

Test results obtained by testing some compounds of the invention will appear from the following table I.

TABLE 1

| Compound | $ED_{50}$ (mg/kg) |
|---|---|
| Compound 2 | 1.5 |
| Compound 4 | 1.4 |
| Compound 6 | 2.5 |

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to thirty (30) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05-100 mg in a pharmaceutically-acceptable carrier per unit dosage.

A typical tablet which may be prepared by conventional tabletting techniques contains:

| Active compound | 1.0 mg |
| --- | --- |
| Lactosum | 67.8 mg Ph. Eur. |
| Avicel ® | 31.4 mg |
| Amberlite ® IRP 88 | 1.0 mg |
| Magnesii stearas | 0.25 mg Ph. Eur. |

Due to their high degree of affinity for the benzodiazepin receptors, the compounds of the invention are extremely useful in the treatment of central nervous system ailments or disorders, when administered in an amount effective for the alleviation, amelioration, or elimination thereof. The important CNS activity of the compounds of the invention includes both anticonvulsant and anxiolytic activities along with a low toxicity, together presenting a most favorable therapeutic index. The compounds of the invention may accordingly be administered to a subject, e.g., a living animal or a human body, in need of the same for the treatment, alleviation, amelioration, or elimination of an indication, associated with the central nervous system and the socalled benzodiazepin receptors, which requires such psychopharmaceutical treatment, e.g., especially convulsion and/or anxiety states, if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their benzodiazepine receptor affinity. Suitable dosage ranges are 1-200 milligrams daily, 1-100 milligrams daily, and especially 1-30 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1

5-tert-butyl-4,5-dihydro-3-(4,4-dimethyl-1,3-dioxopentyl)-4-oxo-imidazo[1,5-a]quinoxaline To a stirred mixture of ethyl 5-tert-butyl-4,5-dihydro-4-oxo-imidazo[1,5-a]quinoxaline-3-carboxylate (1.6 g, 5 mmol) and pinacolone (1.25 ml, 10 mmol) in dry tetrahydrofuran (THF) (30 ml) was added sodium hydride (200 mg, 80% in mineral oil, 6.9 mmol). The mixture was brought to reflux for 2 h, then cooled to room temperature and neutralized with acetic acid. After evaporation of the solvent the residue was partitioned between sat. aqueous NaHCO₃ (10 ml) and methylene chloride (30 ml). The organic phase was dried over Na₂SO₄ and evaporated to give the title compound as yellow crystals. M.p. 190°-191 ° C. (Compound 1).

From the appropriate methyl ketones and ethyl imidazoquinoxalinecarboxylates the following 1,3-diketones were prepared:

3-(3-cyclopropyl-1,3-dioxopropyl)-4,5-dihydro-5-isopropyl-4-oxo-imidazo[1,5-a]quinoxaline, m.p. 210°-212° C. from reaction between cyclopropyl methyl ketone and ethyl 4,5-dihydro-5-isopropyl-4-oxo-imidazo[1,5-a]quinoxaline-3-carboxylate. (Compound 2).

6-chloro-3-(3-cyclopropyl-1,3-dioxopropyl)-4,5-dihydro-5-methyl-4-oxo-imidazo[1,5-a]quinoxaline. M.p. 189°-190° C. from reaction between cyclopropyl methyl ketone and ethyl 6-chloro-4,5-dihydro-5-methyl-4-oxo-imidazo[1,5-a]quinoxaline-3-carboxylate. (Compound 3).

4,5-dihydro-5-isopropyl-4-oxo-3-(1,3-dioxobutyl)-imidazo-[1,5-a]quinoxaline, m.p. 216°-218° C. from reaction between acetone and ethyl 4,5-dihydro-5-isopropyl-4-oxo-imidazo-[1,5-a]quinoxaline-3-carboxylate. (Compound 4).

5-tert-butyl-4,5-dihydro-4-oxo-3-(1,3-dioxobutyl)-imidazo-[1,5-a]quinoxaline, m.p. 175°-177° C. from reaction between acetone and ethyl 5-tert-butyl-4,5-dihydro-4-oxo-imidazo-[1,5-a]quinoxaline-3-carboxylate. (Compound 5).

5-tert-butyl-3-(3-cyclopropyl-1,3-dioxopropyl)-4,5-dihydro-4-oxo-imidazo[1,5-a]quinoxaline, m.p. 175°-178° C. from reaction between cyclopropyl methyl ketone and ethyl 5-tert-butyl-4,5-dihydro-4-oxo-imidazo[1,5-a]quinoxaline-3-carboxylate. (Compound 6).

EXAMPLE 2

3-(3-cyclopropyl-2-methyl-1,3-dioxopropyl)-4,5-dihydro-5-isopropyl-4-oxo-imidazo[1,5-a]quinoxaline Sodium hydride (0.8 g, 60% in mineral oil) was added to a stirred solution of cyclopropyl methyl ketone (1.12 ml, 12 mmol) in dry THF (40 ml). Then ethyl 4,5-dihydro-5-isopropyl-4-oxo-imidazo[1,5-a]quinoxaline-3-carboxylate (3 g, 10 mmol) was added and the mixture was heated at reflux for 30 min. The resulting solution was cooled to room temperature and an excess of methyl iodide (1.4 ml) was added. After stirring overnight the mixture was neutralized with acetic acid and the solvent was evaporated. The residue was triturated with a mixture of ether and water and the precipitate was collected by filtration, rinsed with saturated aqueous NaHCO₃, recrystallized from isopropyl alcohol and finally purified by column chromatography (SiO₂/dichloromethane-acetone 4:1), m.p. 167°-169° C. (Compound 7).

We claim:
1. A compound of formula I

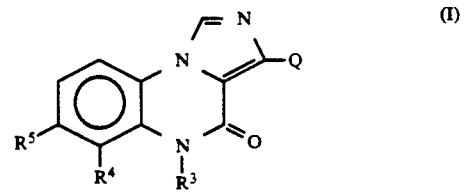

-continued
wherein

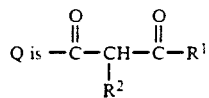

wherein $R^1$ and $R^2$ independently are hydrogen, straight or branched $C_{1-6}$-alkyl or $C_{3-7}$-cycloalkyl;

$R^3$ is hydrogen, straight or branched $C_{1-6}$-alkyl, straight or branched $C_{2-6}$-alkenyl, or aralkyl or aroylalkyl, the latter two may be optionally substituted with halogen or $C_{1-6}$-alkoxy; and $R^4$ and $R^5$ independently are hydrogen, halogen, $C_{1-6}$-alkyl or trifluoromethyl.

2. A compound which is 4,5-dihydro-5-isopropyl-4-oxo-3-(1,3-dioxobutyl)-imidazo[1,5-a]quinoxaline.

3. A compound which is 3-(3-cyclopropyl-1,3-dioxopropyl)-4,5-dihydro-5-isopropyl-4-oxo-imidazo[1,5-a]quinoxaline.

4. A compound which is 5-tert-butyl-3-(3-cyclopropyl-1,3-dioxopropyl)-4,5-dihydro-4-oxo-imidazo[1,5-a]quinoxaline.

5. A pharmaceutical composition comprising a compound according to claim 1 together with a pharmaceutically-acceptable carrier or diluent.

6. A pharmaceutical composition according to claim 5 in the form of an oral dosage unit containing 1-100 mg of the active compound.

7. A method of treating convulsions or anxiety in a subject in need thereof comprising administering to said subject an effective amount of a compound according to claim 1.

8. A method of treating convulsions or anxiety in a subject in need thereof comprising administering to said subject a pharmaceutical composition according to claim 5.

* * * * *